United States Patent [19]

Kronenthal

[11] Patent Number: 4,501,697

[45] Date of Patent: Feb. 26, 1985

[54] 4-[[(AMIDOMETHYL)OXY]METHYL]-2-OXO-1-AZETIDINESULFONIC ACID SALTS

[75] Inventor: David Kronenthal, Yardley, Pa.

[73] Assignee: E. R. Squibb & Sons, Inc., Princeton, N.J.

[21] Appl. No.: 505,547

[22] Filed: Jun. 17, 1983

[51] Int. Cl.³ .................. C07D 205/08; C07D 403/12; C07D 403/13; C07D 401/12
[52] U.S. Cl. ............................ 260/245.4; 260/239 A; 544/359; 546/275
[58] Field of Search ........................ 260/245.4, 239 A; 546/275; 544/359

[56] References Cited

FOREIGN PATENT DOCUMENTS

| | | |
|---|---|---|
| 53816 | 6/1982 | European Pat. Off. . |
| 73061 | 8/1982 | European Pat. Off. . |
| 3239157 | 5/1983 | Fed. Rep. of Germany . |
| 2071650 | 9/1981 | United Kingdom . |

Primary Examiner—Mark L. Berch
Attorney, Agent, or Firm—Lawrence S. Levinson; Donald J. Barrack

[57] ABSTRACT

Antibacterial activity is exhibited by β-lactams having the formula

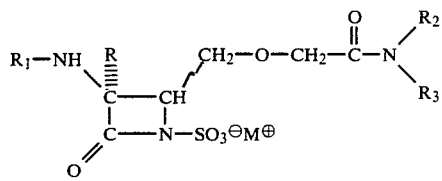

wherein
R is hydrogen or methoxy;
$R_1$ is an acyl group derived from a carboxylic acid;
$R_2$ and $R_3$ are each independently hydrogen, alkyl, or aryl or $R_2$ and $R_3$ when taken together with the nitrogen atom to which they are attached are

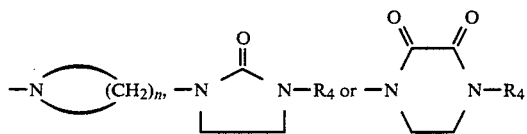

wherein n is 4 or 5 and $R_4$ is hydrogen, alkyl or amino; and
$M^\oplus$ is hydrogen or a cation.

11 Claims, No Drawings

4-[[(AMIDOMETHYL)OXY]METHYL]-2-OXO-1-AZETIDINESULFONIC ACID SALTS

RELATED APPLICATION

United States patent application Ser. No. 308,229, filed Oct. 5, 1981, discloses as antibacterial agents, β-lactams having a sulfonic acid salt substituent in the 1-position, an amino or acylamino substituent in the 3-position, and in the 4-position, a group having the formula —CH$_2$—O—R$_a$ wherein R$_a$ can be, inter alia, alkoxycarbonylalkyl.

BACKGROUND OF THE INVENTION

United Kingdom patent application No. 2,071,650, discloses that β-lactams having a sulfonic acid salt substituent (—SO$_3$$^\ominus$M$^\oplus$, wherein M$^\oplus$ is hydrogen or a cation) in the 1-position and an acylamino substituent in the 3-position, have antibacterial activity. Claim 17 of the patent application discloses δ-lactams having the formula

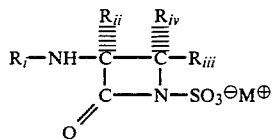

wherein R$_i$ is acyl; R$_{ii}$ is hydrogen or alkoxy of 1 to 4 carbon atoms; R$_{iii}$ and R$_{iv}$ are the same or different and each is hydrogen or alkyl, cycloalkyl or phenyl; and in addition where one of R$_{iii}$ or R$_{iv}$ is hydrogen, the other can be alkenyl, styryl, alkynyl, alkoxy, alkylthio, carboxyl or an alkyl ester thereof, hydroxymethyl, lower alkylsulfonylmethyl, phenylsulfonylmethyl, wherein the phenyl group may be substituted with methyl or halogen, halomethyl, mercaptomethyl or a benzyl or triphenylmethylthio derivative thereof, azidomethyl and aminomethyl; and M$^\oplus$ is hydrogen or a cation.

European patent application No. 0-053-816 discloses antibacterial β-lactams having the formula

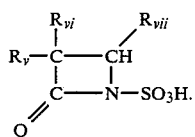

and salts thereof, wherein R$_v$ is inter alia, acylamino, R$_{vi}$ is hydrogen or methoxy and R$_{vii}$ is a "a residue derived from an organic compound by removal of one hydrogen atom attached to a carbon atom thereof". More specifically, R$_{vii}$ can be, inter alia, —CH$_2$—O—CH$_3$ (examples 41 and 47).

BRIEF DESCRIPTION OF THE INVENTION

Antibacterial activity is exhibited by β-lactams having the formula

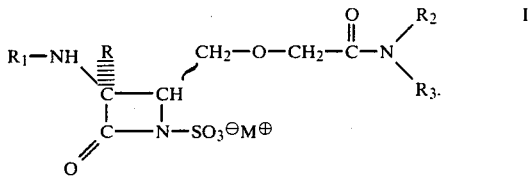

In formula I, and throughout the specification, the symbols are as defined below.

R is hydrogen or methoxy;
R$_1$ is acyl;
R$_2$ and R$_3$ are each independently hydrogen, alkyl, or aryl or R$_2$ and R$_3$ when taken together with the nitrogen atom to which they are attached are

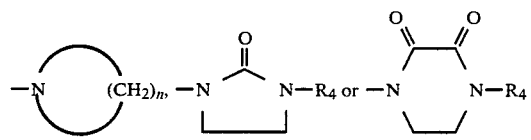

wherein n is 4 or 5, and R$_4$ is hydrogen, alkyl or amino; and
M$^\oplus$ is hydrogen or a cation.

Listed below are definitions of various terms used to describe the β-lactams of this invention. These definitions apply to the terms as they are used throughout the specification (unless they are otherwise limited in specific instances) either individually or as part of a larger group.

The term "aryl" refers to phenyl and phenyl substituted with 1, 2 or 3 amino (—NH$_2$), halogen, hydroxyl, trifluoromethyl, alkyl (of 1 to 4 carbon atoms), alkoxy (of 1 to 4 carbon atoms) or carboxyl groups.

The terms "alkyl" and "alkoxy" refer to both straight and branched chain groups. Those groups having 1 to 10 carbon atoms are preferred, and those groups having 1 to 4 carbon atoms are most preferred.

The terms "alkanoyl" and "alkenyl" refer to both straight and branched chain groups. Those groups having 2 to 10 carbon atoms are preferred.

The terms "cycloalkyl" and "cycloalkenyl" refer to groups having 3, 4, 5, 6 or 7 carbon atoms.

The term "protected carboxyl" refers to a carboxyl group which has been esterified with a conventional ester protecting group. These groups are well known in the art; see, for example, U.S. Pat. No. 4,144,222, issued Mar. 3, 1979. The preferred protected carboxyl groups are benzyl, benzyhydryl and t-butyl esters.

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian patent No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British patent No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

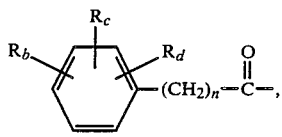

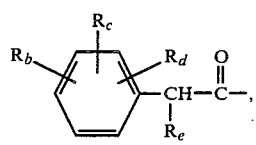

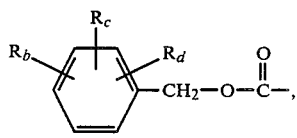

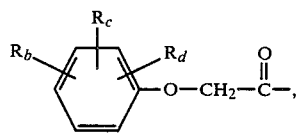

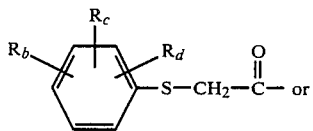

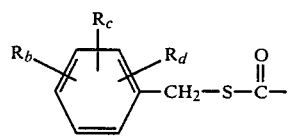

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

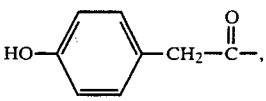

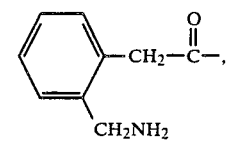

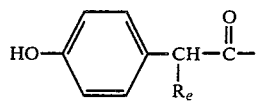

($R_e$ is preferably a carboxyl salt or sulfo salt) and

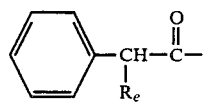

($R_e$ is preferably a carboxyl salt or sulfo salt).

(c) Heteroaromatic groups having the formula

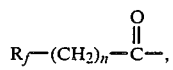

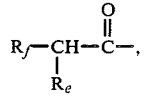

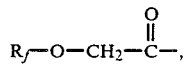

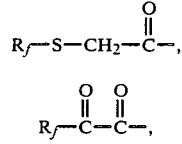

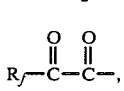

wherein n is 0, 1, 2 or 3; $R_e$ is as defined above; and $R_f$ is a substituted or unsubstituted 5-, 6- or 7-membered heterocyclic ring containing 1,2,3 or 4 (perferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl or 1 to 4 carbon atoms, alkoxy of 1 to 4 carbon atoms, or

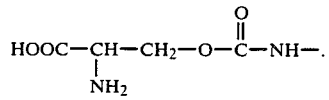

Preferred heterocyclic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

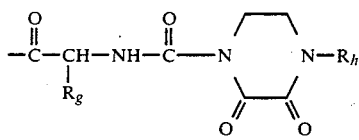

wherein $R_g$ is an aromatic group (including carbocyclic aromatics such as those of the formula

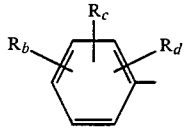

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

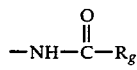

wherein $R_g$ is as defined above) or alkylcarbonylamino.

Preferred [[(4-substituted-2,3-dioxo-1-piperazinyl)-carbonyl]amino]arylacetyl groups include those wherein $R_h$ is ethyl, phenylmethyleneamino or 2-furylmethyleneamino.

(e) (Substituted oxyimino)arylacetyl groups having the formula

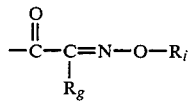

wherein $R_g$ is as defined above and $R_i$ is hydrogen, alkyl, cycloalkyl, alkylaminocarbonyl, arylaminocarbonyl (i.e.,

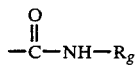

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acrylamino)arylacetyl groups having the formula

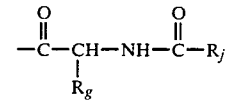

wherein $R_g$ is as defined above and $R_j$ is

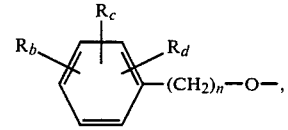

amino, alkylamino, (cyanoalkyl)amino, amido, alkylamido, (cycloalkyl)amido,

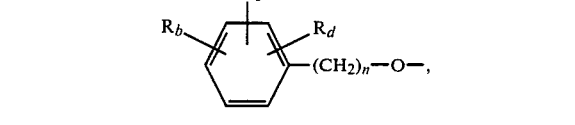

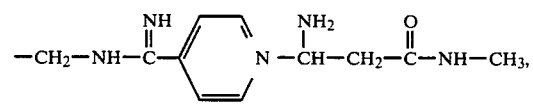

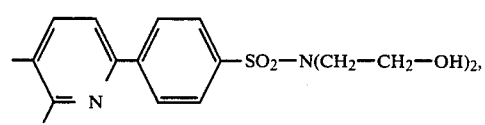

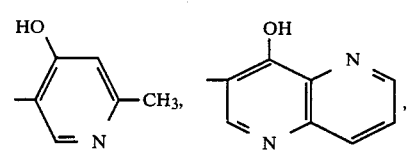

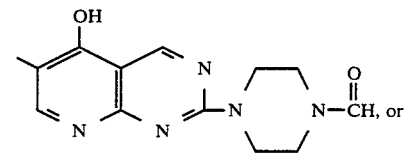

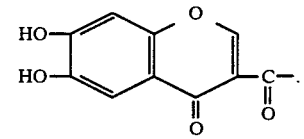

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

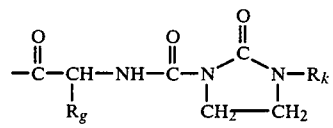

wherein $R_g$ is as defined above and $R_k$ is hydrogen, alkylsulfonyl, arylmethyleneamino (i.e., —N=CH—$R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The term "cation", as used throughout the specification, refers to any positively charged atom or group of atoms. The "$-SO_3^{\ominus}M^{\oplus}$" substituent on the nitrogen atom of the β-lactams of this invention encompasses all sulfonic acid salts. Pharmaceutically acceptable salts are, of course, preferred, although other salts are also useful in purifying the products of this invention or as intermediates for the preparation of pharmaceutically acceptable salts. The cationic portion of the sulfonic acid salts of this invention can be obtained from either organic or inorganic bases. Such cationic portion includes, but is not limited to, the following ions: ammonium; substituted ammonium, such as alkylammonium (e.g., tetra-n-butylammonium, referred to hereinafter as tetrabutylammonium); alkali metal, such as lithium, sodium and potassium; alkaline earth metal, such as calcium and magnesium; pyridinium; dicyclohexylammonium; hydrabaminium; benzathinium; N-methyl-D-glucaminium.

As set forth in formula I, and in the definitions following formula I, $M^{\oplus}$ can be hydrogen. Such compounds are often referred to in the art as "inner salts" by virtue of a positive and negative charge in the molecule.

This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C). However, these compounds can be prepared as enantiomeric mixtures containing both the active and inactive epimers. This invention encompasses the enantiomeric mixture, as well as any other composition containing the isomers with the absolute configuration specified above.

DETAILED DESCRIPTION OF THE INVENTION

The β-lactams of formula I have activity against a range of gram-negative and gram-positive organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel β-lactams of this invention. Such methods of administration include oral, intravenous, intramuscular, and as a suppository.

The compounds of this invention wherein the 4-substituent is in the beta-configuration can be prepared from a β-lactam having the formula

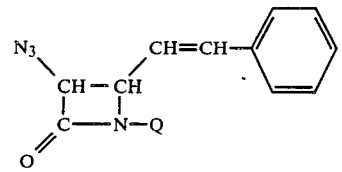

wherein Q is

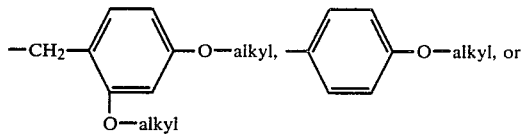

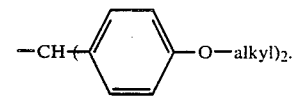

While styryl is shown in formula II as the preferred 4-substituent, other olefins can also be used. Ozonolysis of a compound of formula II followed by reduction yields the corresponding compound having the formula

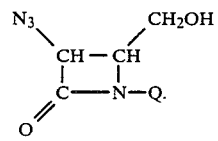

Reduction is preferably accomplished using a chemical reducing agent such as sodium borohydride.

Treatment of a compound of formula III with a non-nucleophilic base, such as sodium hydride, followed by reaction with a compound having the formula

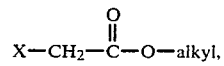

wherein X is a leaving group such as a halogen, tosylate, mesylate, etc., yields the corresponding compound having the formula

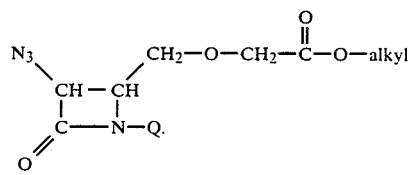

Oxidative removal of the 1-substituent of a compound of formula V can be accomplished by treating the compound with ceric ammonium nitrate, yielding the corresponding compound having the formula

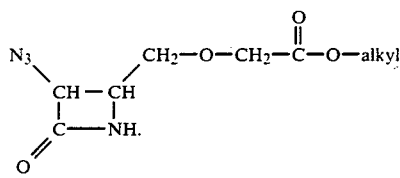

Alternatively, oxidative removal of the 1-substituent of a compound of formula V can be accomplished by treating the compound with acid if

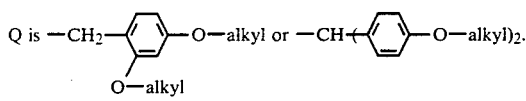

Cleavage of the ester group of the 4-substituent of a compound of formula VI can be accomplished by treatment with base or acid and yields the compound having the formula

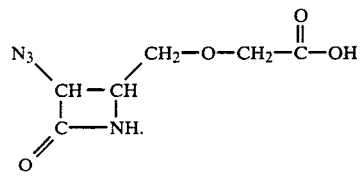

Before adding the $-SO_3^{\ominus}M^{\oplus}$ substituent to the 1-position of a compound of formula VII, the carboxyl group in the 4-substituent must first be protected. This is preferably accomplished by reaction with a diazomethane, preferably diphenyl diazomethane, to yield the compound having the formula

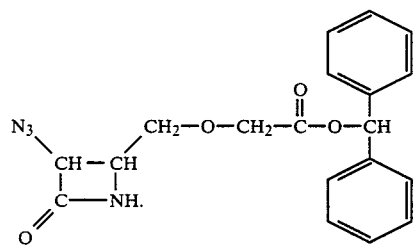

Introduction of the sulfo substituent onto a compound of formula VIII yields a compound having the formula

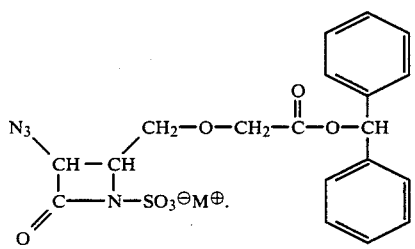

This is accomplished by reacting a compound of formula VIII with a complex of pyridine and sulfur trioxide. The reaction can be run in an organic solvent or in a mixture of organic solvents, preferably a mixture of a polar solvent such as dimethylformamide and a halogenated hydrocarbon such as dichloromethane. This reaction yields a compound of formula IX wherein $M^{\oplus}$ is pyridinium ion. Instead of using a pre-formed complex of pyridine and sulfur trioxide, the complex can be formed in situ, e.g., using chlorosulfonyltrimethylsilyl ester and pyridine as reagents. Alternatively, a complex of dimethylformamide-sulfur trioxide, 2-picoline-sulfur trioxide or 2,6-lutidine-sulfur trioxide can be used.

Using conventional techniques (e.g., ion-exchange resins, or ion-pair extraction) the pyridinium salt formed by the above procedure can be converted to other salts. These techniques can also be used to convert the products of formula I, or any of the intermediates described herein, to other salts.

A second method for introducing the sulfo group to the 1-position of an azetidine of formula VIII comprises first silylating the compound and then subjecting the silated compound to a silyl interchange reaction. Exemplary silylating agents are monosilyltrifluoroacetamide, trimethylsilylchloride/triethylamine, and bis-trimethylsilyltrifluoroacetamide, and an exemplary reagent useful for the silyl interchange reaction is trimethylsilyl chlorosulfate.

Deprotection of the carboxyl group of the 4-substituent of formula IX yields the compound having the formula

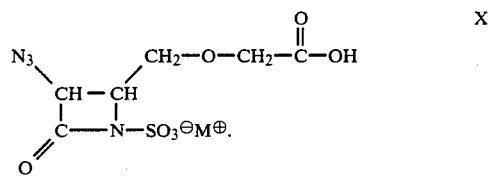

Removal of the diphenylmethane group can be accomplished using trifluoroacetic acid in anisole.

Conversion of the 4-substituent of a compound of formula X to the corresponding acid halide (preferably acid chloride) can be accomplished using art-recognized procedures. For example, a compound of formula X can be treated with oxalyl chloride to yield

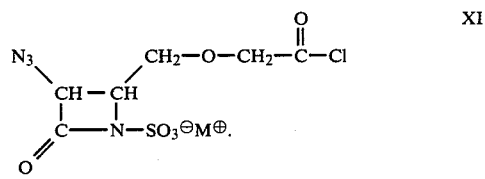

Reaction of a compound of formula XI with a silyl compound having the formula

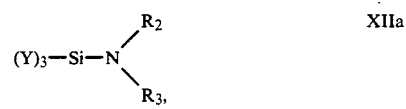

wherein Y is methyl, or with an amine having the formula

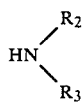 XIIb yields the corresponding compound having the formula

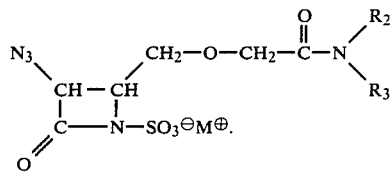 XIII

A compound of formula XIII can be converted to the corresponding compound having the formula

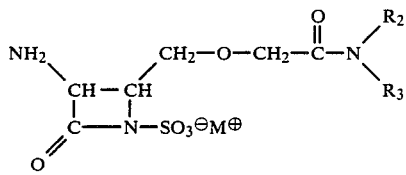 XIV by hydrogenolysis. Other techniques include reduction with zinc, and treatment with triphenylphoshpine followed by hydrolysis of the resulting iminophosphorane.

Conventional acylation techniques can be used to prepare the products of formula I from a zwitterion of formula XIV. Exemplary acylation techniques include reaction with a carboxylic acid ($R_1$—OH), or corresponding carboxylic acid halide or carboxylic acid anhydride. The reaction with a carboxylic acid proceeds most readily in the presence of a carbodiimide and a substance capable of forming an active ester in situ such as N-hydroxybenzotriazole. In those instances where the acyl group ($R_1$) contains reactive functionality (such as amino or carboxyl groups) it may be necessary to first protect those functional groups, then carry out the acylation reaction, and finally deprotect the resulting product.

Alternatively, those compounds of formula I, can be prepared by first activating the carboxyl group of a compound of formula X using art recognized procedures. Exemplary of such procedures is the treatment of a compound of formula X with an organic base such as triethylamine, followed by reaction with diphenylchlorophosphate, to yield the compound having the formula

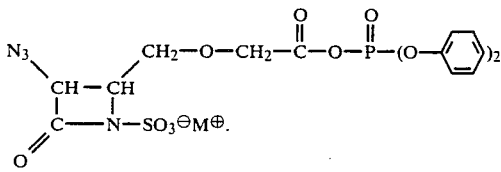 XV

The compound of formula XV can be reacted with ammonium hydroxide, or any primary or secondary amine, to yield the compound of formula XIII. Treatment of a compound of formula XIII as described above will yield the corresponding product of formula I.

Those compounds of formula I wherein the 4-substituent is in the alpha-configuration can be prepared by first reacting a primary amine having the formula

Q—NH$_2$     XVI with an aldehyde having the formula

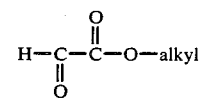 XVII to yield the corresponding Schiff base. A [2+2] cycloaddition reaction of the Schiff base with an activated form of α-phthalimidoacetic acid yields a compound having the formula

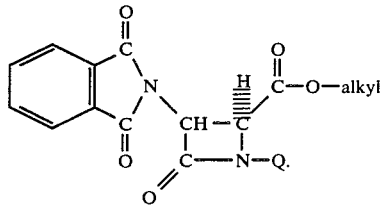 XVIII

Treatment of a compound of formula XVII with base yields the corresponding compound having the formula

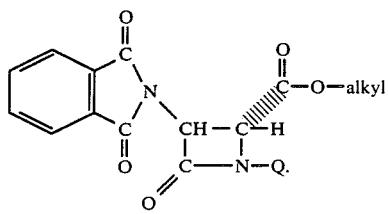 XIX

Reaction of a compound of formula XIX with a reagent such as methyl hydrazine (to cleave the phthaloyl group), followed by the introduction of a protecting group on the 3-nitrogen substituent yields the corresponding compound having the formula

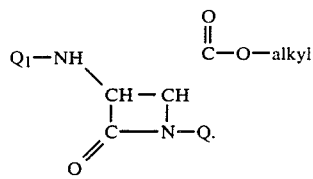 XX wherein $Q_1$ is a nitrogen protecting group, e.g., benzyloxycarbonyl or t-butoxycarbonyl.

Reduction of the ester moiety of the 4-substituent of the compound of formula XX, e.g., by chemical reduction using sodium borohydride, yields the corresponding compound having the formula

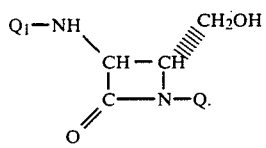

If the group Q₁—NH in a compound of formula XXI contains urethane functionality (e.g., $Q_1$ is a benzyloxycarbonyl or t-butoxycarbonyl group), the introduction of an acetic acid ester group (c.f. the conversion of formula III to formula IV) can be effected with a diazoacetate under non-basic conditions. The resulting compound can be converted to a compound having the formula

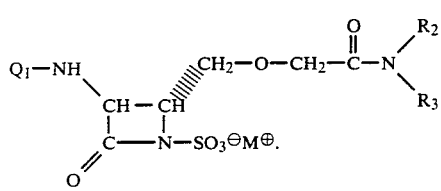

utilizing the sequential procedures described above for the conversion of a compound of formula V to a compound of formula XIII.

Deprotection of a compound of formula XXII yields a zwitterion having the formula

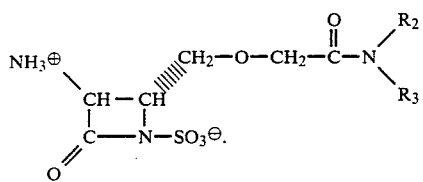

The deprotection techniques used are conventional, and will depend on the particular protecting group ($Q_1$) present. Treatment with acid (e.g., formic acid or trifluoroacetic acid) cleaves a triphenylmethyl or t-butoxycarbonyl protecting group. A benzyloxycarbonyl protecting group can be cleaved by catalytic hydrogenation. Treatment with phosgene or phosphorous pentachloride cleaves an amide protecting group.

Conventional acylation techniques can be used to convert a zwitterion of formula XXIII to a product of formula I. These techniques have been described above for the conversion of a zwitterion of formula XIII to a product of formula I.

The β-lactams of formula I wherein R is methoxy can be prepared from the corresponding compound having the formula

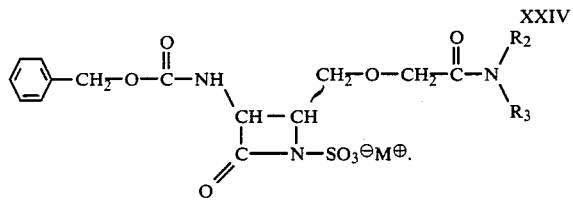

Halogenation of the urethane nitrogen of a compound of the above formula yields the corresponding compound having the formula

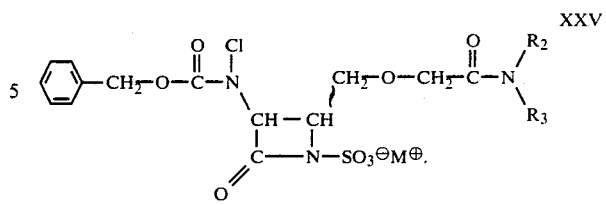

Reaction of an intermediate of formula XXV with a methoxylating agent, e.g., an alkali metal methoxide yields a compound having the formula

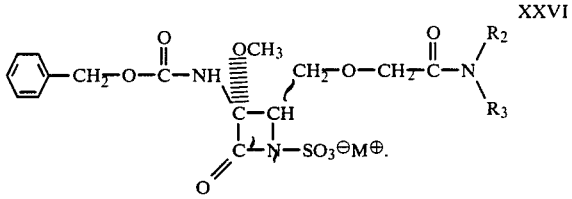

The reaction can be run in an organic solvent, e.g., a polar organic solvent such as dimethylformamide, at a reduced temperature.

Removal of the benzyloxycarbonyl group from a compound of formula XXVI followed by acylation yields the desired product of formula I wherein R is methoxy.

The following examples are specific embodiments of this invention.

EXAMPLE 1

[3α(Z),4α]-4-[(2-Amino-2-oxoethoxy)methyl]-3-[[(2-amino-4-thiazolyl)(methoxyimino)acetyl]-2-oxo-1-azetidinesulfonic acid, monopotassium salt (A) (±)-(cis)-3-Azido-4-hydroxymethyl-1-(4-methoxyphenyl)-2-oxoazetidine A solution of (cis)-3-azido-1-(4-methoxyphenyl)-4-(2-phenylethenyl)-2-oxoazetidine (6 g, 18.75 mmole) in 1:1 ethanol-dichloromethane (180 ml) was cooled to −78° C. and ozonized until the mixture retained a purple hue. The reaction was purged with nitrogen, and sodium borohydride (2.835 g, 75 mmole) was added as a solid followed by 85 ml of ethanol. The mixture is allowed to stand at −78° C. for five minutes and then stirred at ice-bath temperature for one hour. The reaction was acidified to pH 4 with 3N hydrochloric acid, and the solvents were removed in vacuo. The residue was partitioned between water and ethyl acetate. The aqueous layer was extracted with additional ethyl acetate and the organic extracts were washed with saturated potassium bicarbonate, brine, dried (sodium sulfate), filtered, and concentrated to a solid which was treated with ether. After standing under ether for three hours at 5° C., the white solid was filtered, washed with fresh ether, hexane, and dried under high vacuum. The yield of the title compound was 3.333 g.

(B) .(±)-(cis)-[(3-Azido-1-(4-methoxyphenyl)-2-oxo-4-azetidinyl)methoxy]acetic acid, methyl ester A suspension of 60% sodium hydride (749 mg, 18.72 mmole) was washed under argon with hexane (9 ml). The sodium hydride was then cooled to −20° C. and dimethylformamide (20 ml) was added. The mixture was then cooled to −50° C. and methyl bromoacetate (1.77 ml, 18.72 mmole) was added via syringe. Next, a solution of (±)-(cis)-3-azido-4-hydroxymethyl-1-(4-methoxyphenyl)-2-oxoazetidine (3.303 g, 13.37 mmole) in dimethylformamide (25 ml) was added dropwise. The reaction was stirred at −50° C. for ten minutes, warmed to −20° C. over 40 minutes, stirred at this temperature for thirty minutes, and then stirred at −5° C. overnight (ca. sixteen hours). The solvent was mostly removed in vacuo (30° C.). The residue was treated with ether, then pH 4.5 monobasic potassium phosphate buffer. The aqueous layer was extracted with additional ether. The organic extracts were washed with cold 0.5N hydrochloric acid, water, brine, dried (sodium sulfate), and filtered and concentrated to 4.2 g of an orange oil. The crude product was chromatographed on silica gel (180 g, 230–400 mesh) eluting with 60% hexane-ethyl acetate. Combination of fractions 35–46 (20 ml fractions), concentration and drying in vacuo produced 2.46 g of the title compond as an oil.

(C) (±)-(cis)-[(3-Azido-2-oxo-4-azetidinyl)methoxy]acetic acid, methyl ester

A solution of (±)-(cis)-[(3-azido-1-(4-methoxyphenyl)-2-oxo-4-azetidinyl)methoxy]acetic acid, methyl ester (2.054 g, 6.44 mmole) in acetonitrile (40 ml) was cooled to −5° C. A solution of ceric ammonium nitrate (10.62 g, 19.32 mmole) in water (30 ml) was added rapidly over ca. forty-five seconds. The reaction was warmed to +10° C. over fifteen minutes, diluted with water (100 ml), and extracted with ethyl acetate (two 80 ml portions). Sodium chloride was added to the aqueous layer which was again extracted with ethyl acetate (ca. 150 ml). The organic extracts were washed with saturated potassium bicarbonate, saturated sodium sulfite solution, brine, and dried (sodium sulfate). Filtration followed by solvent removal yielded 1.56 g of crude product which was chromatographed on silica gel (55 g, 230–400 mesh). Elution with 70% ethyl acetate-hexane yielded 1.1 g of the title compound as a heavy oil.

(D) (±)-(cis)-[(3-Azido-2-oxo-4-azetidinyl)methoxy]acetic acid

A solution of potassium carbonate (7.335 g, 53.08 mmole) in water (80 ml) was cooled to 0° C. and deoxygenated with argon. A solution of (±)-(cis)-[(3-azido-2-oxo-4-azetidinyl)methoxy]acetic acid, methyl ester (2.261 g, 10.62 mmole) in tetrahydrofuran (60 ml) was added and the mixture stirred at 0° C. for five minutes and then at room temperature for 5.5 hours. The reaction was cooled and acidified with 6N hydrochloric acid to pH 7. The tetrahydrofuran was mostly removed in vacuo, and the aqueous residue (pH ca. 8) was extracted with ethyl acetate. The aqueous layer was cooled to 0° C., acidified with 6N hydrochloric acid to pH 2, saturated with sodium chloride, and extracted with ethyl acetate (fifteen 80 ml portions). The organic extracts were dried (sodium sulfate), filtered, and concentrated in vacuo. The yield of crude acid was 1.503 g.

(E) (±)-(cis)-[(3-Azido-2-oxo-4-azetidinyl)methoxy]acetic acid diphenylmethyl ester A solution of (±)-(cis)-[(3-azido-2-oxo-4-azetidinyl)methoxy]acetic acid (0.880 g, 4.42 mmole) was treated with a solution of diphenyl diazomethane (858 mg, 4.42 mmole) in acetone (12 ml). The reaction was stirred at room temperature for nineteen hours and then combined with another run (621 mg acid, 3.12 mmole). The solvent was removed in vacuo and ethyl acetate was added and evaporated. The residue was dissolved in ethyl acetate (70 ml), dried (sodium sulfate), filtered, and concentrated to 2.6 g of a heavy yellow-red oil. The crude product was chromatographed on silica gel (230–400 mesh, 100 g) with 50% hexane-ethyl acetate. Concentration of the appropriate fractions and removal of solvents produced a heavy oil which was triturated with ether to produce a white solid which was filtered and dried to yield 1.34 g of the title compound. An additional 463 mg was obtained from the mother liquor. The total yield was 1.804 g.

(F) (±)-(cis)-[(3-Azido-1-sulfo-2-oxo-4-azetidinyl)methoxy]acetic acid, potassium salt, diphenylmethyl ester A solution of (±)-(cis)-[(3-azido-2-oxo-4-azetidinyl)methoxy]acetic acid, diphenylmethyl ester (500 mg, 1.37 mmole) and pyridine-sulfur trioxide complex (870 mg, 5.48 mmole) in dimethylformamide (5 ml) was stirred under argon at 50° C. for seventy-five minutes. The reaction was cooled and the dimethylformamide was removed in vacuo at 30° C. The residue was treated with 70 ml of pH 5.5 monobasic potassium phosphate (0.5M) and the resulting mixture was stirred for thirty minutes. The white insoluble material was isolated by centrifugation, washed with water, and dissolved in acetonitrile. The solvent was evaporated, and the residue treated with toluene. The solvent was evaporated and the residue (foam) was triturated with ether-hexane. Removal of solvent produced a white solid which was dried at 70° C. (high vacuum) over phosphorus pentoxide for two hours. The yield of the title compound was 605 mg.

(G) (±)-(cis)-[(3-azido-1-sulfo-2-oxo-4-azetidinyl)methoxy]acetic acid, potassium salt A solution of (±)-(cis)-[(3-Azido-1-sulfo-2-oxo-4-azetidinyl)methoxy]acetic acid, potassium salt, diphenylmethyl ester (605 mg, 1.346 mmole) in anisole (5.6 ml) was cooled to −30° C. under argon and treated with trifluoroacetic acid (12.4 ml) dropwise over ca. seven minutes. The reaction was warmed to −10° C. and stirred at this temperature for ninety minutes. The mixture was cooled to −15° C. and treated sequentially with ether (35 ml) and hexane (18 ml) producing a white precipitate. The mixture was stirred at −15° C. for fifteen minutes and then at room temperature for fifteen minutes. The white solid was isolated by centrifugation and washed with ether and hexane. The crude product was dried at room temperature in vacuo (ca. 20 mm of Hg) overnight and then at 65° C. (high vacuum, phosphorous pentoxide) for several hours. The yield of the title compound was 375 mg.

(H) (±)(cis)-4-[(2-Amino-2-oxoethoxy)methyl]-3-azido-2-oxo-1-azetidinesulfonic acid, potassium salt A solution of (±)-(cis)-[(3-azido-1-sulfo-2-oxo-4-azetidinyl)methoxy]acetic acid, potassium salt (150 mg, 0.472 mmole) in dimethylformamide (0.75 ml) was treated with triethylamine (150 l, 1.079 mmole), stirred under argon at room temperature for ten minutes, and cooled to −30° C. Diphenylchlorophosphate (205 l, 0.99 mmole) was added, the reaction was warmed to −25° C., stirred at this temperature for twenty-five minutes, and cooled to −30° C. An aqueous solution of ammonium chloride (257 l of a 1M solution), triethylamine, (150 l), and concentrated ammonium hydroxide (72 l, 1.08 mmole) was added rapidly dropwise, followed by 400 l of dimethylformamide. The reaction was warmed to −25° C. stirred for twenty-five minutes and warmed to −15° C. to −20° C. and stirred for twenty-five minutes. The solvent was removed in vacuo (from −15° C. to 25° C.), and the residue treated with water (some insolubles), and applied to a Dowex K+ ion-exchange resin (40 ml). Elution with water (5 ml fractions) produced 175 mg of a white solid from fractions 7 and 8. This material was chromatographed on HP-20 (80 ml), eluting with water (5 ml fractions). Fractions 11–20 were combined and evaporated to an oil which was triturated with acetonitrile, producing a white solid. The acetonitrile was removed in vacuo, and the crude product was dried overnight in vacuo at 55° C. over phosphorous pentoxide. The yield of the title compound was 73 mg.

(I) [3α(Z),4α]-4-[(2-Amino-2-oxoethoxy)methyl]-3-[[(2-amino-4-thiazolyl)-(methoxyimino)acetyl]amino]-2-oxo-1-azetidinesulfonic acid, monopotassium salt A solution of (±)-(cis)-4-[(2-amino-2-oxoethoxy)methyl]-3-azido-2-oxo-1-azetidinesulfonic acid, potassium salt (35 mg, 0.1104 mmole) in dimethylformamide-methanol (1:3, ca. 2 ml) was stirred under 1 atmosphere of hydrogen in the presence of 10% palladium on charcoal (12 mg) for ninety minutes. The mixture was diluted with methanol, centrifuged, and the supernatant was removed. The catalyst was washed several additional times in this manner with methanol. The combined supernatants were concentrated in vacuo (25° C.) and the residue was treated with dimethylformamide (2 ml). The solvent was removed at 27° C. under high vacuum and 2 ml dimethylformamide were added to the residue. The dimethylformamide solution was added to a mixture of N-hydroxybenzotriazole hydrate (17 mg, 0.11M mmole), (Z)-2-amino-α-(methoxyimino)-4-thiazoleacetic acid (22 mg, 0.1104 mmole), and dicyclohexylcarbodiimide (23 mg, 0.1104 mmole, added last) that had stirred under argon for forty minutes. The reaction was stirred for seventy hours at room temperature. The solvent was removed in vacuo at 28° C. The residue was treated with water, the insolubles were removed by centrifugation and washed with additional water. The combined supernatants were concentrated in vacuo and passed through a 40 ml HP-20 column (water elution). Combination and evaporation of the appropriate fractions followed by drying at 60° C. over phosphorous pentoxide (high vacuum, two hours) afforded 25 mg of the title compound.

What is claimed is:

1. A compound having the formula

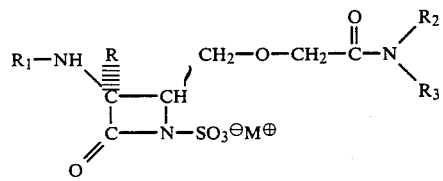

wherein

R is hydrogen or methoxy;

$R_1$ is an acyl group derived from a carboxylic acid;

$R_2$ and $R_3$ are each independently hydrogen, alkyl, phenyl or phenyl substituted with 1, 2 or 3 amino, halogen, hydroxyl, trifluoromethyl, alkyl of 1 to 4 carbon atoms, alkoxy of 1 to 4 carbon atoms or carboxyl groups, or $R_2$ and $R_3$ when taken together with the nitrogen atom to which they are attached are

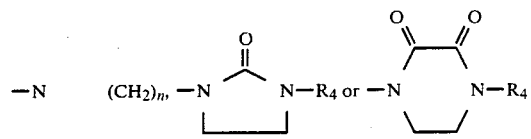

wherein n is 4 or 5 and $R_4$ is hydrogen, alkyl or amino; and $M^{\oplus}$ is hydrogen or a pharmaceutically acceptable cation;

wherein the term "alkyl" refers to groups having 1 to 10 carbon atoms.

2. A compound in accordance with claim 1 wherein R is hydrogen.

3. A compound in accordance with claim 1 wherein $R_2$ and $R_3$ are each hydrogen.

4. A compound in accordance with claim 2 wherein $R_2$ and $R_3$ are each hydrogen.

5. A compound in accordance with claim 1 wherein $R_1$ is

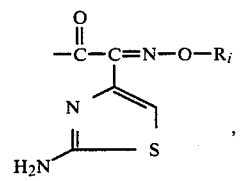

and $R_i$ is methyl, ethyl, carboxymethyl, 1-carboxy-1-methylethyl, 2,2,2-trifluoroethyl or 2-carboxycyclopropyl.

6. A compound in accordance with claim 2 wherein $R_1$ is

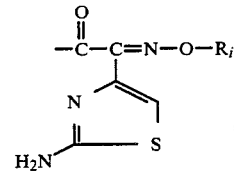

and $R_i$ is methyl, ethyl, carboxymethyl, 1-carboxy-1-methylethyl, 2,2,2-trifluoroethyl or 2-carboxycyclopropyl.

7. A compound in accordance with claim 1 wherein $R_1$ is

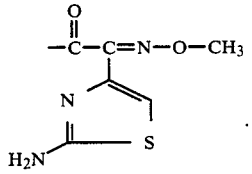

8. A compound in accordance with claim 2 wherein $R_1$ is

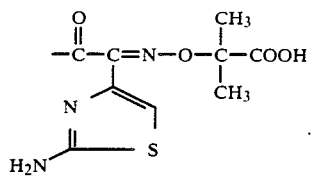
10. A compound in accordance with claim 2 wherein R₁ is
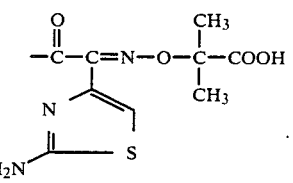
9. A compound in accordance with claim 1 wherein
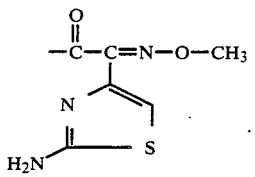
R₁ is
11. The compound in accordance with claim 1, [3α(Z),4α]-4-[(2-amino-2-oxoethoxy)methyl]-3-[[(2-amino-4-thiazolyl)(methoxyimino)acetyl]-2-oxo-1-azetidinesulfonic acid, or a pharmaceutically acceptable salt thereof.
* * * * *